(12) United States Patent
Leschinsky et al.

(10) Patent No.: US 9,713,480 B2
(45) Date of Patent: Jul. 25, 2017

(54) ANASTOMOSIS PROBE AND CUTTING DEVICE

(71) Applicant: Empire Technology Development LLC, Wilmington, DE (US)

(72) Inventors: Boris Leschinsky, Mahwah, NJ (US); Jonathan R. Williams, Montville, NJ (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 684 days.

(21) Appl. No.: 14/356,391

(22) PCT Filed: Sep. 16, 2013

(86) PCT No.: PCT/US2013/060016
§ 371 (c)(1),
(2) Date: May 5, 2014

(87) PCT Pub. No.: WO2015/038168
PCT Pub. Date: Mar. 19, 2015

(65) Prior Publication Data
US 2015/0105810 A1    Apr. 16, 2015

(51) Int. Cl.
*A61B 5/026*    (2006.01)
*A61B 17/32*    (2006.01)
(Continued)

(52) U.S. Cl.
CPC ...... *A61B 17/32002* (2013.01); *A61B 5/0261* (2013.01); *A61B 17/320016* (2013.01);
(Continued)

(58) Field of Classification Search
CPC ....... A61B 5/026–5/0295; A61B 6/461–6/466; A61B 17/11–17/1146;
(Continued)

(56) References Cited

U.S. PATENT DOCUMENTS 5,738,096 A    4/1998  Ben-Haim
5,740,808 A    4/1998  Panescu et al.
(Continued)

OTHER PUBLICATIONS

Chung, R.S., et al., "The role of tissue ischemia in the pathogenesis of anastomotic stricture," Department of Surgery, Veterans Administration Medical Center, vol. 104, No. 5, pp. 824-829, Nov. 1988.
(Continued)

*Primary Examiner* — Victor Nguyen
*Assistant Examiner* — Jonathan Hollm
(74) *Attorney, Agent, or Firm* — Turk IP Law, LLC

(57) ABSTRACT

Technologies are provided for an opto-mechanical device for enabling surgeons to rapidly simulate proposed intestinal/colorectal anastomosis cut lines and assess their impact upon tissue perfusion prior to their implementation. The pre-selection process enables a surgeon to decide upon the locations of the anastomotic cut lines that are most likely to reduce ischemia, while preserving most of the intestinal tissue length. The opto-mechanical device may simulate a cut line by applying pressure to intestinal tissue and detecting a light pattern transmitted through the intestinal tissue before and after the applied pressure. A perfusion map may be generated to estimate perfusion quality around the circumference of the intestinal tissue at the site of a simulated cut line, and the perfusion map may be displayed as a two-dimensional graphic image of the proposed anastomosis site. Once the site of the best cut line is selected, the surgeon may activate a cutting blade to implement the cut.

7 Claims, 8 Drawing Sheets

(51) Int. Cl.
  *A61B 17/11* (2006.01)
  *A61B 17/00* (2006.01)
  *A61B 90/00* (2016.01)

(52) U.S. Cl.
  CPC . *A61B 17/1114* (2013.01); *A61B 2017/00057* (2013.01); *A61B 2017/00061* (2013.01); *A61B 2017/00066* (2013.01); *A61B 2090/0811* (2016.02); *A61B 2562/046* (2013.01)

(58) Field of Classification Search
  CPC .................. A61B 17/115–17/1155; A61B 2017/1103–2017/1142; A61B 2017/1157
  See application file for complete search history.

(56) References Cited

U.S. PATENT DOCUMENTS

| | | |
|---|---|---|
| 5,970,982 A | 10/1999 | Perkins |
| 2005/0197534 A1 | 9/2005 | Barbato et al. |
| 2009/0105734 A1 | 4/2009 | Gronberg et al. |
| 2009/0234248 A1* | 9/2009 | Zand .................. A61B 5/0031 600/587 |
| 2010/0168557 A1 | 7/2010 | Deno et al. |

OTHER PUBLICATIONS

Karliczek, A., "Intraoperative assessment of microperfusion with visible light spectroscopy for prediction of anastomotic leakage in colorectal anastomoses," Colorectal Disease, vol. 12, Issue 10, pp. 1018-1025, Oct. 2010.

Karliczek, A., "Intraoperative ischemia of the distal end of colon anastomoses as detected with visible light spectroscopy causes reduction of anastomotic strength," The Journal of Surgical Research, vol. 152, Issue 2, pp. 288-295, Apr. 2009.

Kudszus, S., "Intraoperative laser fluorescence angiography in colorectal surgery: a noninvasive analysis to reduce the rate of anastomotic leakage," Langenbeck's Archives of Surgery, vol. 395, Issue 8, pp. 1025-1030 (2010).

Myers, C., et al., "Real-time probe measurement of tissue oxygenation during gastrointestinal stapling: mucosal ischemia occurs and is not influenced by staple height" vol. 23, Issue 10, pp. 2345-2350, Oct. 2009.

Urbanavičius, L., "How to assess intestinal viability during surgery: a review of techniques," World J Gastrointest Surg, vol. 3, Issue 5, pp. 59-69, May 2011.

International Search Report and Written Opinion for PCT/US2013/060016, filed on Sep. 16, 2013, mailed on Jan. 9, 2014.

* cited by examiner

ANASTOMOSIS PROBE AND CUTTING DEVICE

CROSS-REFERENCE TO RELATED APPLICATION

This Application is a U.S. National Stage filing under 35 U.S.C. §371 of PCT Application Ser. No. PCT/US13/60016 filed on Sep. 16, 2013. The contents of the PCT Application are herein incorporated by reference in its entirety.

BACKGROUND

Unless otherwise indicated herein, the materials described in this section are not prior art to the claims in this application and are not admitted to be prior art by inclusion in this section.

It is often necessary to resect a portion of the colon or intestine in order to remove a tumor or to treat a chronic infection. Following the resection, an anastomosis may be performed to reconnect remaining intestinal tissue to restore function. During the anastomosis procedure, the surgeon examines the cut ends of the intestine prior to suturing them together. Upon this examination, the surgeon may choose to re-cut the ends to completely assure that all cancerous or infected tissue will be excluded from the planned anastomosis while trying to conserve as much intestinal tissue with viable microcirculation as possible. In these cases, the surgeon's judgment is subjective. It is difficult to visually assess the impact of the resection upon local blood flow (especially microcirculation), and particularly around its complete circumference, which may create a significant surgical risk for the patient.

Specifically, ischemia of the tissue at the site of the anastomosis is often correlated with subsequent leakage and associated infection. Reported incidences of anastomotic leakage range between 1.2% and 19.2% of patients and up to 32% of patients with anastomotic leakage die from the postoperative complication. The risk of anastomotic leakage can be reduced by selecting an intestinal cut and suture line that preserves macro and micro circulation and adequate perfusion of the tissue on both sides of the anastomosis.

SUMMARY

The following summary is illustrative only and is not intended to be in any way limiting. In addition to the illustrative aspects, embodiments, and features described above, further aspects, embodiments, and features will become apparent by reference to the drawings and the following detailed description.

According to some examples, the present disclosure generally describes a probe cutting device for selecting a location to cut intestines for anastomosis. The probe cutting device may include a substantially cylindrical probe having a substantially rounded distal tip, a plurality of light emitters positioned circumferentially on an external surface of the probe in a vicinity of a distal end of the probe, a sliding member having a hollow center, the sliding member configured to lit concentrically around the probe and to slide axially along a longitudinal axis of the probe, and a plurality of photodetectors positioned circumferentially around an interior surface of the sliding member, where the plurality of photodetectors are oriented to face the plurality of light emitters when the sliding member is slid over the probe.

According to other examples, the present disclosure describes a method of simulating a cut line in intestinal wall tissue and cutting along the cut line for achieving anastomosis. The method may include making an initial incision in intestinal wall tissue near a location of tissue to be removed from intestines, inserting a probe including a plurality of light emitters positioned circumferentially on an external surface of the probe in a vicinity near a distal end of the probe through the incision into a lumen of the intestines such that the intestinal wall tissue surrounds the external surface of the probe and covers the plurality of light emitters, sliding a sliding member over the probe and an external surface of the intestinal wall tissue to a potential out line at a location where a plurality of photodetectors positioned circumferentially around an interior surface of the sliding member are oriented to face the plurality of light emitters, compressing a compression ring positioned around a circumference of the sliding member to simulate cutting along the potential cut line, transmitting a light pattern detected at the potential cut line to an external computing device, generating a perfusion map based on the detected light pattern at the potential cut line, and if the perfusion map indicates that the potential cut line is an acceptable cut line, activating a cutting blade positioned next to the compression ring on the sliding member to cut the intestinal wall tissue along the potential cut line.

According to further examples, the present disclosure also describes a system for simulating a cut line in intestinal wall tissue and cutting along the cut line for achieving anastomosis. The system may include a substantially cylindrical probe having a substantially rounded distal tip, a plurality of light emitters positioned circumferentially on an external surface of the probe in a vicinity of a distal end of the probe, a sliding member having a hollow center, the sliding member configured to fit concentrically around the probe and to slide axially along a longitudinal axis of the probe, a plurality of photodetectors positioned circumferentially around an interior surface of the sliding member, where the plurality of photodetectors may be oriented to face the plurality of light emitters when the sliding member is slid over the probe, an external computing device configured to generate a perfusion map based on a detected light pattern, and a monitor associated with the external computing device configured to display the generated perfusion map.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
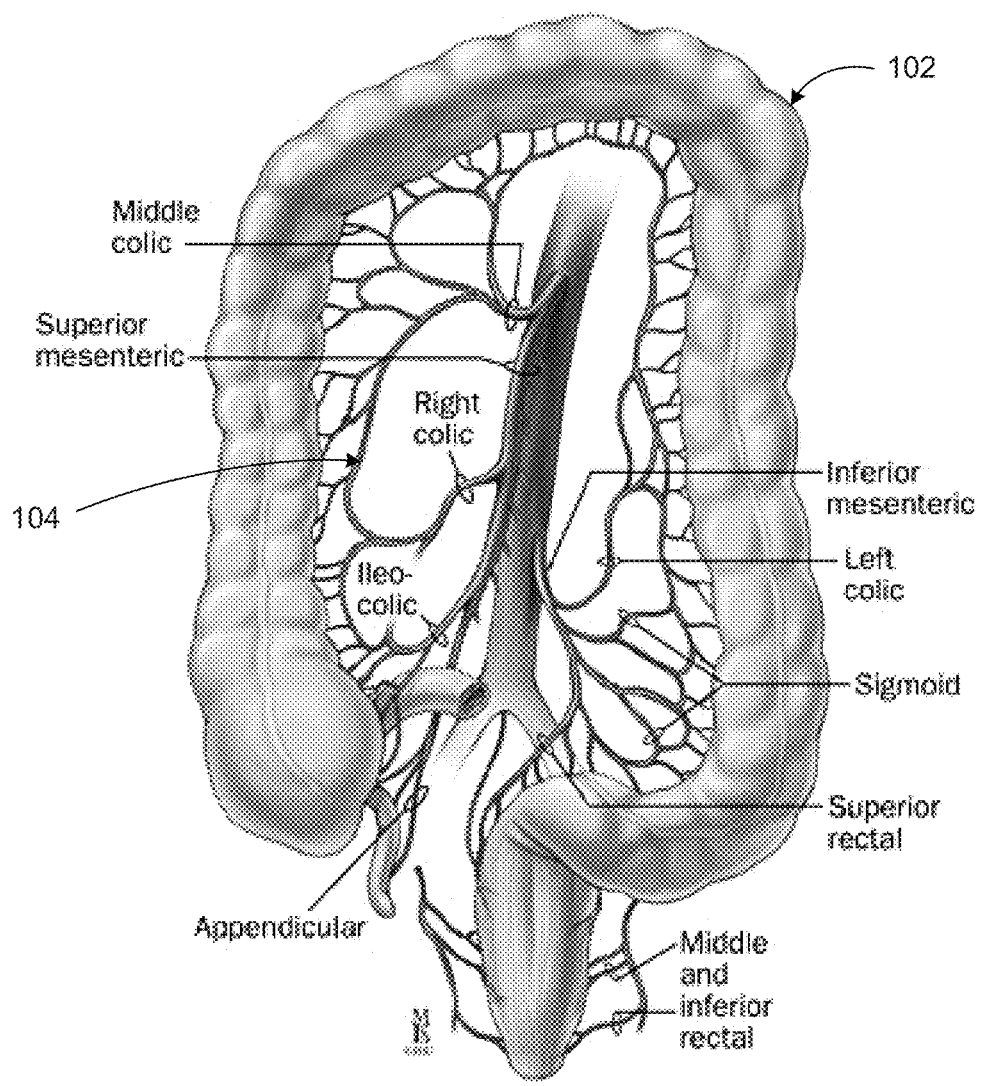
FIG. 1 illustrates an example anatomical layout of the intestines and associated blood vessel network.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to compositions, methods, apparatus, systems, and/or devices related to providing a device for simulating and selecting an anastomosis cut line.

Briefly stated, an opto-mechanical device is provided for enabling surgeons to rapidly simulate proposed intestinal/colorectal anastomosis cut lines and assess their impact upon tissue perfusion prior to their implementation. The pre-selection process enables a surgeon to decide upon the locations of the anastomotic cut lines that are most likely to reduce ischemia, while preserving most of the intestinal tissue length. The opto-mechanical device may simulate a cut line by applying pressure to intestinal tissue and detecting a light pattern transmitted through the intestinal tissue before and after the applied pressure. A perfusion map may be generated to estimate perfusion quality around the circumference of the intestinal tissue at the site of a simulated cut line, and the perfusion map may be displayed as a two-dimensional graphic image of the proposed anastomosis site. Once the site of the best cut line is selected, the surgeon may activate a cutting blade to implement the cut.

FIG. 1 illustrates an example anatomical layout of the large intestines and the associated blood vessels that form a circulatory supply to the intestines, arranged in accordance with at least some embodiments as described herein. The large intestines 102, or the colon, encompass a large network of blood vessels 104, which form a circulatory supply to the intestines. Often times a portion of the intestines may need to be surgically removed, or resected, to treat chronic infections and to remove tumors. After the resection, an anastomosis procedure may be performed to reconnect remaining intestinal tissue.

During the anastomosis procedure, the surgeon may need to re-cut the ends of the intestines 102 to ensure that the diseased tissue will be excluded from the anastomosis, while trying to conserve as much intestinal tissue with microcirculation as possible. It is difficult to visually assess the impact of the resection upon local blood flow, including microcirculation, and the small arteries of the network of blood vessels 104 may be inadvertently cut during the resection procedure, causing local blood impairment and ischemia.

Figure 2:
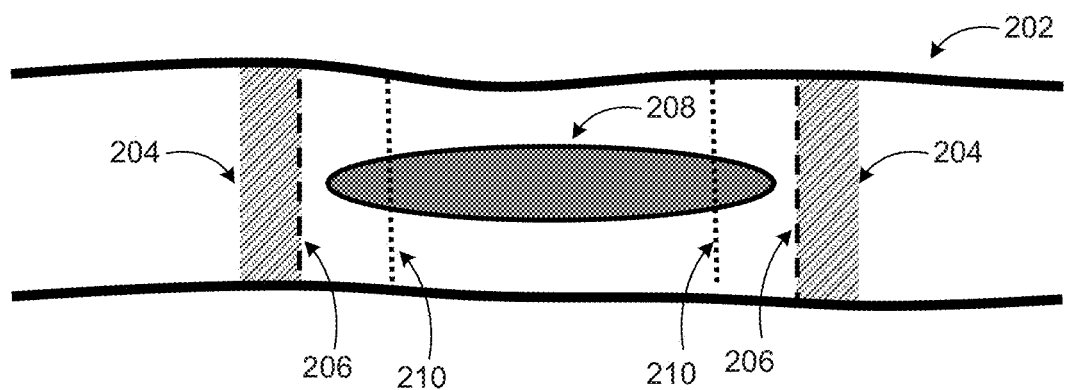
FIG. 2 illustrates an example portion of the intestines including potential cutting regions.

FIG. 2 illustrates an example portion of the intestines including potential cutting regions, arranged in accordance with at least some embodiments as described herein.

A surgical procedure associated with preparing the intestines for an anastomosis may include identifying a portion of the intestines for removal, such as a colon 202, which may include a tumor 208 or other infection causing a need for tissue removal. In an example embodiment, initial incision lines 210 may be used for insertion of a medical device into a portion of the colon 202 in order to remove or resect the tumor 208. In some scenarios, however, the selected initial incision lines 210 may not include the entirety of the tumor 208, and additional incision lines 206 may choose to exclude additional tumor 208 tissue. While the additional incision lines 206 may exclude additional tissue for removal, the additional initial incision lines 206 may not optimize local perfusion of the intestinal tissue at the incision line.

Utilizing a pre-selection process employing an opto-mechanical device, surgeons may select optimal incision lines that may facilitate enabling the surgeon to remove most or all of the tumor 208, while preserving local perfusion, reducing ischemia and preserving intestinal tissue length, A final cut line for removing intestinal tissue and performing an anastomosis may be selected from a target zone 204 in order to optimize local perfusion at the site of the cut line. An opto-mechanical device may assist the surgeon in selecting the target zone 204 for the final cut for successful and durable anastomosis.

Figure 3A:
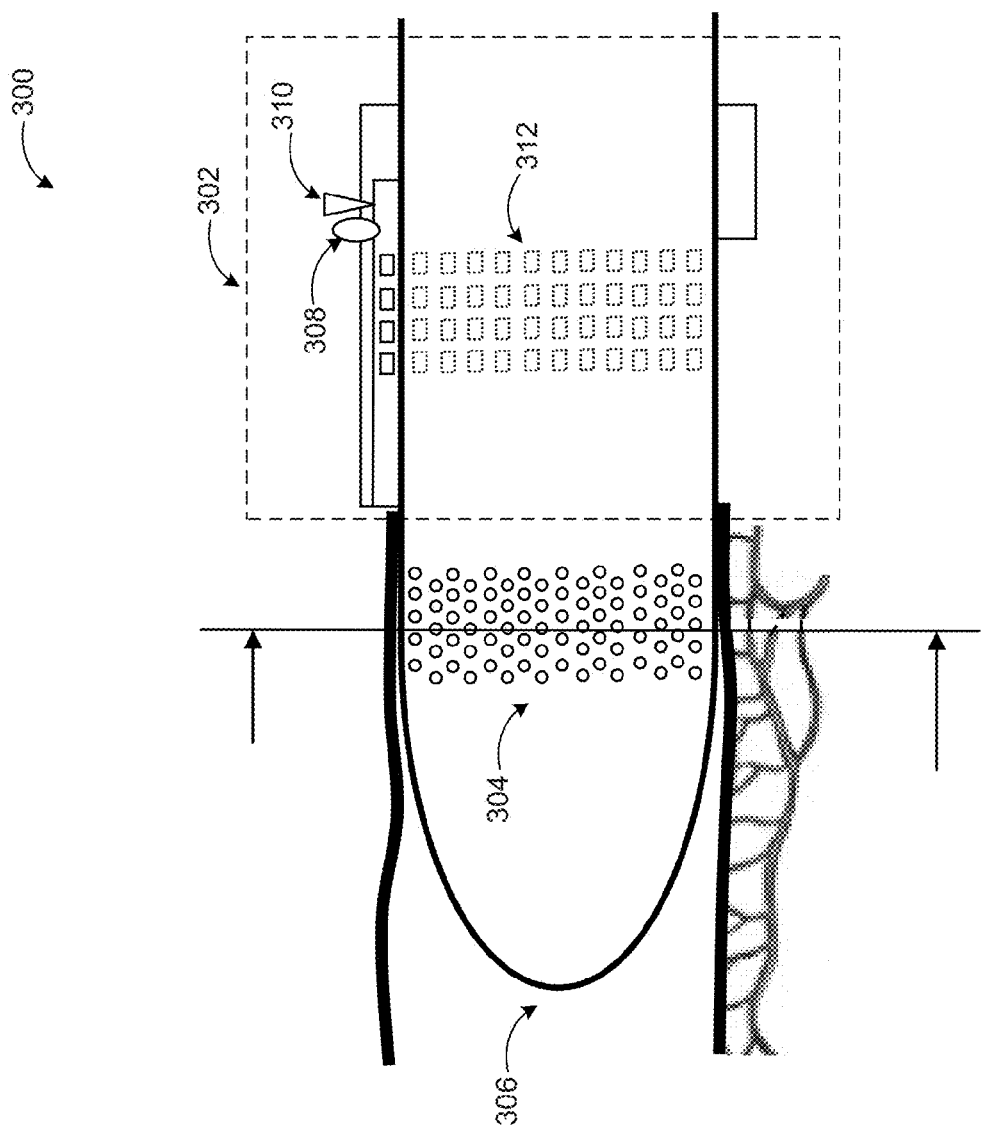
FIGS. 3A and 3B illustrate example cross sections of an opto-mechanical device including a probe and light emitters.

FIG. 3A illustrates a cross section of an example opto-mechanical device including a probe and LED light emitters, arranged in accordance with at least some embodiments as described herein.

In a system according to embodiments, an opto-mechanical device 300 may assist a surgeon in selecting a target zone for an anastomosis by simulating a cutting of the intestines or colon at a potential cut line. The opto-mechanical device 300 may include a probe 306 and a sliding member 302 configured to fit over the probe 306. The probe 306 may include a plurality of light emitting diode (LED) emitters 304 arranged around a circumference of the probe 306. The sliding member 302 may include a compression ring 308, a cutting blade 310, and a plurality of photodetectors 312 arranged around a circumference of the sliding member 302.

In an example scenario for simulating a cutting to select an anastomosis cut line, as will be described in further detail below, the probe 306 may be inserted into an interior space, or lumen, of a transected colon. The sliding member 302 may be slid over the probe 306 and over an external surface of the transected colon, and the compression ring 308 may compress the colon tissue to simulate cutting of the colon tissue. A perfusion map may be generated before and after compression of the compression ring 308 at the potential cut line based on a light pattern detected by the photodetectors 312 in order to determine if the potential cut line may be an acceptable location for performing an anastomosis. If the potential cut line location is determined to be acceptable, the cutting blade 310 may be activated to perform cutting of the colon tissue at the selected cut line location.

In a system according to embodiments, the probe 306 may be configured in a substantial bullet shape, such that the probe 306 may have a substantially rounded tip and a substantially cylindrical body. The bullet shaped probe 306 may be inserted through an initial incision into a lumen of a transected intestine or colon. The initial incision may be at a location near a tumor or infected intestinal tissue identified for removal. The probe 306 may be sized to slightly dilate the intestinal walls to assure close contact with an internal surface of the intestinal walls. The plurality of LED emitters 304 may be positioned circumferentially on an external surface of the probe 306 near a distal end of the probe 306. When the probe 306 is inserted through the incision into a lumen of the intestines, the intestinal wall tissue may surround the external surface of the probe 306 and substantially cover the LED emitters 304.

In an example embodiment, the sliding member 302 may be concentric with the probe 306, and may be moved axially along a length of the probe 306. When the probe 306 is inserted into the lumen of the intestines, the sliding member 302 may be slid over the probe 306 and over an external surface of the intestines such that the intestinal wall tissue may pass between the probe 306 and the sliding member 302. The probe 306 may also include a mechanical stop for defining fully-forward and fully-retracted positions of the sliding member 302 with respect to the probe 306.

The sliding member 302 may be composed from a transparent material to enable visualization of the probe 306 and intestinal tissue when the sliding member 302 is slid over the probe 306 in situ. The sliding member 302 may include a plurality of photodetectors 312 configured to detect light emitted from the LED emitters 304 on the probe 306. The plurality of photodetectors 312 may be positioned circumferentially around an interior surface of the sliding member 302, and the photodetectors 312 may be oriented to face the LED emitters 304 when the probe 306 is inserted into the lumen of the intestines and the sliding member 302 is slid over the probe 306.

In an example embodiment, the photodetectors 312 may be sensors of light or electromagnetic energy, which may be transmitted by the LED emitters 304. The LED emitters 304 positioned around the probe 306 may be configured to emit light radially through the intestinal walls. The LED emitters 304 may include at least one red LED die and at least one infrared (IR) LED die, which may be adjacent to each other in each LED emitter package. The LED emitters may be configured to emit light having a wavelength in a range from about 550 nm to about 900 nm in order to transmit through the intestinal tissue. When the sliding member 302 is slid over the probe 306 such that the photodetectors 312 are in apposition with the LED emitters 304, the photodetectors 312 may be configured to detect a light pattern transmitted by the LED emitters 304.

During operation, the photodetectors 312 may measure light absorbance at two wavelengths from the red LED die and the IR LED die by multiplexing the operation of the LED emitters, that is, by alternately activating a red die, and then activating an IR die. The LED emitters and the photodetectors may multiplex emission and detection of light to reject interference from ambient light sources by interleaving samples of ambient light when the LED emitters are off and subtracting the ambient light from the signals captured when the LED emitters are on. Additionally, multiplexing the emission of light may help to avoid optical cross-talk and to ensure that the photodetectors 312 measure light travelling on a direct radial path through the tissue, that is, from an LED emitter directly below a corresponding photodetector. Furthermore, physically adjacent LED emitter packages may be activated on an alternating basis in order to reduce an effect of light scattering upon the light absorbance readings by the photodetectors 312. This may have an additional advantage of rejecting the effects of local ambient light by continuously interleaving a period when none of the LED emitters are active. From the absorbance readings of ambient light, the magnitude of the ambient light may be estimated and continuously subtracted from the absorbance measurements.

In a system according to embodiments, the compression 308 and the cutting blade 310 on the sliding member 302 may be employed in order to simulate a proposed cut line before performing a cut. The compression ring 308 may be configured to fit concentrically around a circumference of the sliding member 302, and the compression ring 308 may be compressed to apply pressure to intestinal wall tissue simulating a cut. The compression ring 308 may simulate cutting by being compressed to apply a pressure to the intestinal tissue that is greater than an arterial and venous pressure of the intestinal wall tissue. In an example scenario, the photodetectors 312 may be configured to detect a light pattern emitted from the LED emitters 304 before compression of the compression ring 308 and after compression of the compression ring 308 at the potential cut line location. The light patterns detected before and after compression of the compression ring 308 may be utilized to generate a perfusion map at the potential cut line, from which a surgeon may determine if the potential cut line is acceptable.

Figure 3B:
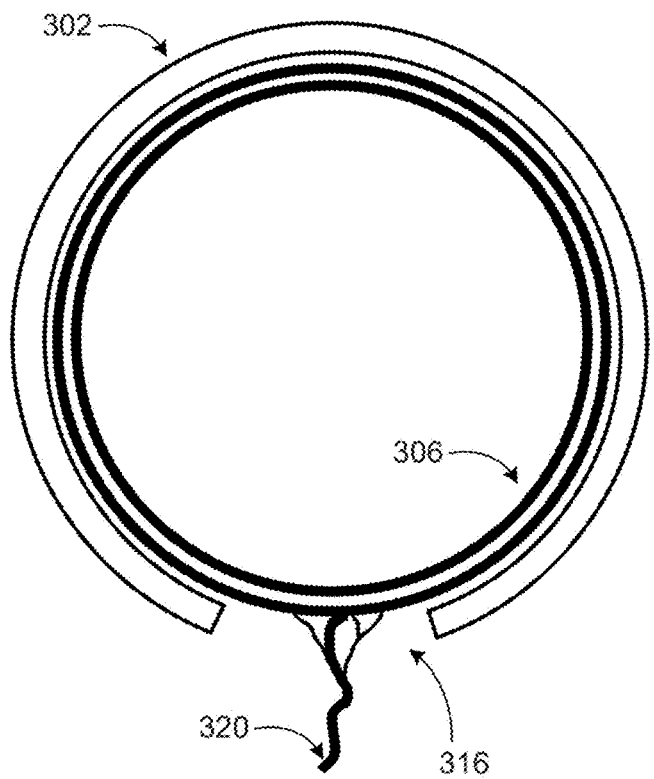

FIG. 3B illustrates a cross-sectional representation of an example probe, arranged in accordance with at least some embodiments as described herein. In FIG. 3B, an opto-mechanical device as described in conjunction with FIG. 3A may include a probe 306 and a sliding member 302 configured to fit concentrically around the probe 306. The probe 306 may be inserted into a lumen of the intestines, and the sliding member 302 may be slid over the probe 306 and over an external surface of the intestines such that the intestinal wall tissue may pass between the probe 306 and the sliding member 302. The intestines may also include mesenteric tissue extending from an external surface of the intestines. The mesenteric tissue may be tissue or peritoneum connecting the parts of the intestine such as the jejunum and ileum to a wall of the abdomen. In a system according to embodiments, the sliding member 302 may include a longitudinal slot along the length of the sliding member 302 in order to accommodate the exit of mesenteric tissue when the sliding member 302 is slid over the external surface of the intestines.

Figure 4:
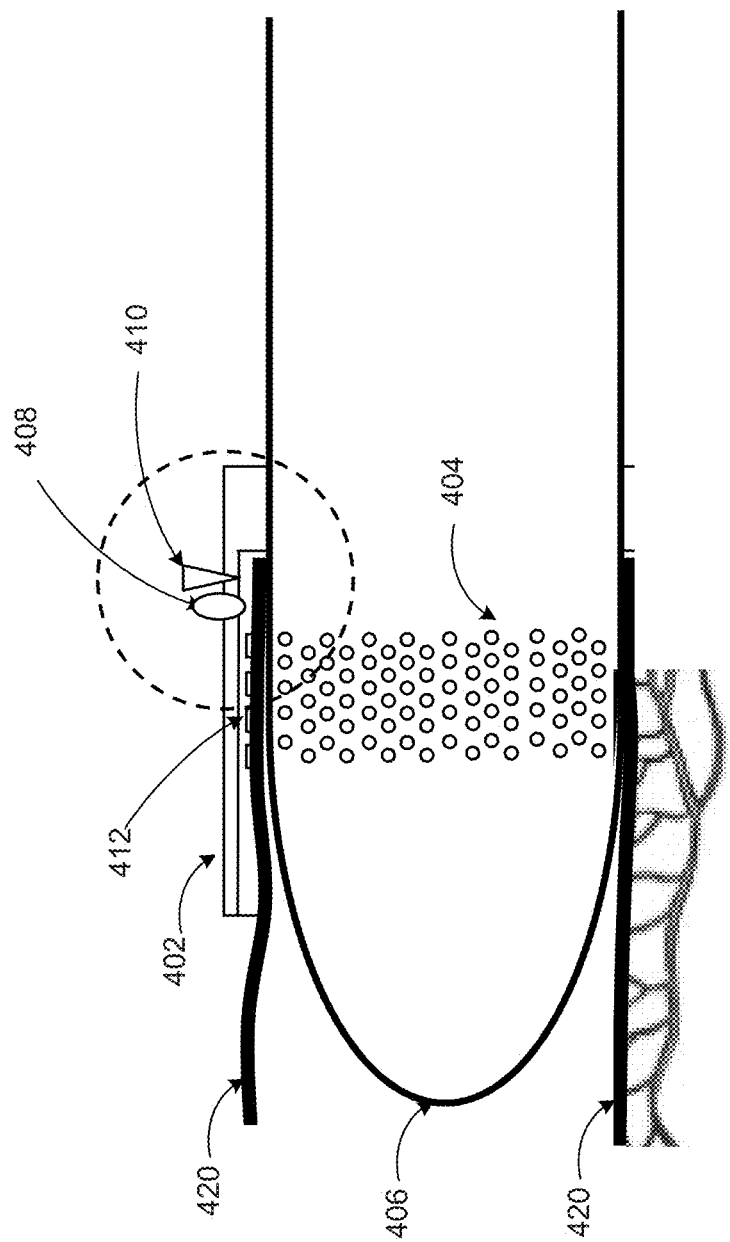
FIG. 4 illustrates an example compression ring and cutting blade on a sliding member.

FIG. 4 illustrates an example compression ring and cutting blade on a sliding member, arranged in accordance with at least some embodiments as described herein. As previously described in conjunction with FIG. 3A, an opto-mechanical device may be employed to assist a surgeon in selecting a cut line for performing an anastomosis that preserves local perfusion. The opto-mechanical device may include a probe 406 and a sliding member 402 configured to slide over the probe 406 and an external surface of intestinal tissue 420. The probe 406 may include a plurality of LED emitters 404 configured to radially transmit light through the intestinal tissue. The sliding member 402 may include a plurality of photodetectors 412 arranged on an interior surface of the sliding member 402 configured to detect the light emitted from the plurality of LED emitters 404 through the intestinal tissue 420. The sliding member 402 may also include a compression ring 408 for applying pressure to the intestinal tissue 420.

In an example scenario for simulating a cut line, the probe 406 may be advanced into the lumen of the intestines until the intestinal tissue 420 eclipses the plurality of LED emitters 404 on the probe 406 at a proposed location for performing an anastomosis of the intestinal tissue 420. The plurality of LED emitters 404 may be illuminated in order to facilitate visualization in situ. The sliding member 402 may be advanced over the probe 406 and intestinal tissue 420 to position the photodetectors 412 over the LED emitters 404 across a range of possible surgical cut lines which may define a target zone range of potential cut lines. In an example scenario, the sliding member 402 may be advanced until it reaches a forward limit mechanical stop included on the opto-mechanical device for defining a fully forward position.

When the sliding member 402 is in a position such that the photodetectors 412 are aligned with the LED emitters 404, an initial perfusion map may be generated based on a light pattern detected by the photodetectors 412 of light emitted by the LED emitters 404 through the intestinal tissue. An external computing device as part of an optical system configured to communicate with the LED emitters 404 and photodetectors 412 may generate the initial perfusion map for determining a local perfusion of the intestinal tissue 420 at the target zone of potential cut lines. After the initial perfusion map has been generated, the compression ring 408 may be activated to simulate a cutting at the potential cut line. During the compression of the compression ring 408, a second perfusion map may be generated by the external computing device based on the light pattern detected during compression. After the light pattern has been detected for generating the second perfusion map, the compression ring 408 may be released to prevent inducing ischemia at the location of the compression.

Figure 5:
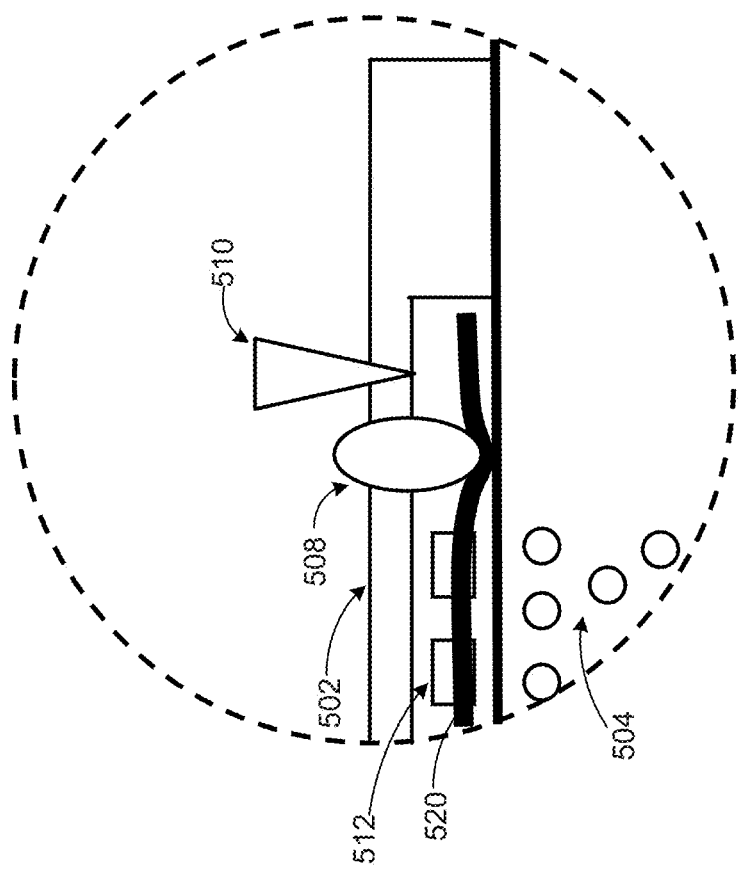
FIG. 5 illustrates compression of a compression ring on a sliding member.

FIG. 5 illustrates compression of the compression ring on a sliding member, arranged in accordance with at least some embodiments as described herein. A compression ring 508 may simulate a cutting of intestinal tissue 520 by compressing the intestinal tissue 520 at a proposed cut line. The compression may apply a sate and reversible degree of circumferential pressure to the intestinal tissue 520 that exceeds an arterial and venous pressure of the intestinal tissue 520 at the potential cut line. A plurality of photodetectors 512 may be configured to detect a light pattern transmitted by LED emitters 504 before compression of the compression ring 508 and during compression of the compression ring 508 at the potential cut line location. The detected light patterns may be transmitted to an external computing device for generation of a perfusion map.

Figure 6:
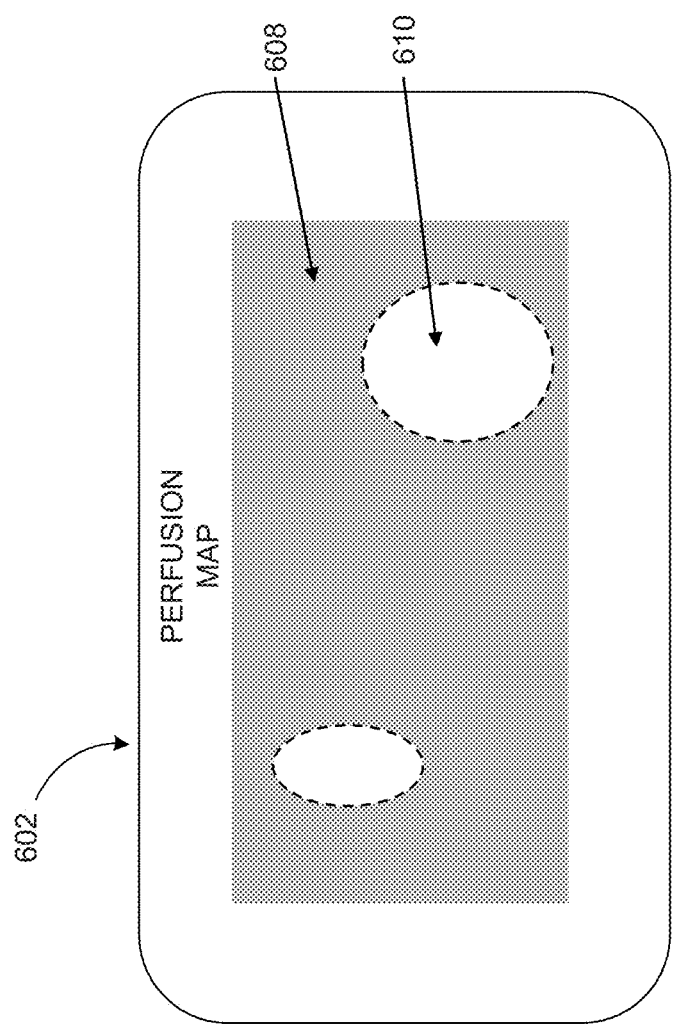
FIG. 6 illustrates an example perfusion map.

FIG. 6 illustrates an example perfusion map, arranged in accordance with at least some embodiments as described herein. As discussed previously, an initial perfusion map may be generated for a potential out line when a sliding member is advanced over a probe to align photodetectors disposed on the sliding member with a plurality of LED emitters disposed on the probe. The initial perfusion map may be generated based on a light pattern detected by the photodetectors from light transmitted through intestinal tissue by the LED emitters. The photodetectors may transmit the detected light pattern to an external computing device configured to generate a perfusion map based on the detected light pattern. The initial perfusion map generated before compression of the intestinal tissue may be utilized as a baseline perfusion map in order to determine a relative perfusion of the intestinal tissue at a potential cut line. Subsequently, the intestinal tissue may be compressed utilizing a compression ring on the sliding member, and a second perfusion map may be generated during the compression.

The external computing device may calculate a relative perfusion at the potential cut line based on the initial perfusion map generated before compression and the second perfusion map generated during compression of the compression ring. Employing a relative perfusion may normalize transmitted light pattern readings and may compensate for local detection variables such as intestinal tissue thickness, ambient light detection, and transmission qualities, for example. The relative perfusion may be computed by a ratio of light transmitted through the intestinal wall tissue before compression is applied to the light transmitted after compression is applied, which may represent a ratio of estimated tissue oxygen saturation before the compression to estimated tissue oxygen saturation after the compression. This computation may be performed on a pixel-to-pixel basis.

According to some embodiments, an example perfusion map 602 may be displayed as a two-dimensional, color-coded graphic image of estimated perfusion quality at the proposed anastomosis site to enable a surgeon to review the estimated perfusion of the intestinal tissue. The perfusion map 602 may display a representation of areas of the intestinal tissue having adequate perfusion 608 and areas having poor perfusion 610 or ischemia. If it is determined, based on the displayed perfusion map 602, that the impact upon local perfusion of the simulated cut at the potential cut line is acceptable, that is, that the area may have adequate perfusion 608, then the surgeon may proceed to perform a cut at the potential cut line employing a cutting blade on the sliding member. If the potential cut line is determined not to be acceptable, then the sliding member and probe may be advanced slightly forward in the intestines to a new proposed cut line, and the process of simulating a cut line employing the compression ring and generating a perfusion map based on a detected light pattern may be repeated. Furthermore, the process of simulating and selecting a cut line for anastomosis may be employed on both sides of an anastomosis, that is, after completion of a cut on a first side, the probe may be moved to the other side.

In another example embodiment, the perfusion map for estimating tissue oxygen saturation may be generated based on the detected light patterns based on spectrographic means. Specifically, the method may rely upon a known difference in optical absorbance of oxyhemoglobin ($HbO_2$) with respect to de-oxyhemoglobin (Hb) in the blood and intestinal tissue. $HbO_2$ absorbs less light than Hb in a red region of the spectrum. The difference in absorbance of these materials may be on the order of 10:1 when measured with a light at 660 nm. The relative proportions of a mixture of $HbO_2$ and Hb (i.e., % saturation) can be estimated by computing the ratio of the relative absorbance of the mixture at two different wavelengths, e.g., 660 nm and 805 nm. The absorbance measurement at 805 nm may be performed in order to normalize the mixture's measurement. The optical absorbance of Hb and $HbO_2$ are identical at the 805 nm wavelength, such that the intensity the transmitted light at this wavelength is not a function of saturation. As discussed previously the LED emitters may contain two adjacent emitting LED dies (one red and one IR) and may transmit light in a range from about 550 nm to about 900 nm. A light pattern may be generated based on the transmission of the light through the intestinal tissue, and the perfusion map may be generated based on the detected light pattern and the known light absorbances of Hb and $HbO_2$.

Figure 7:
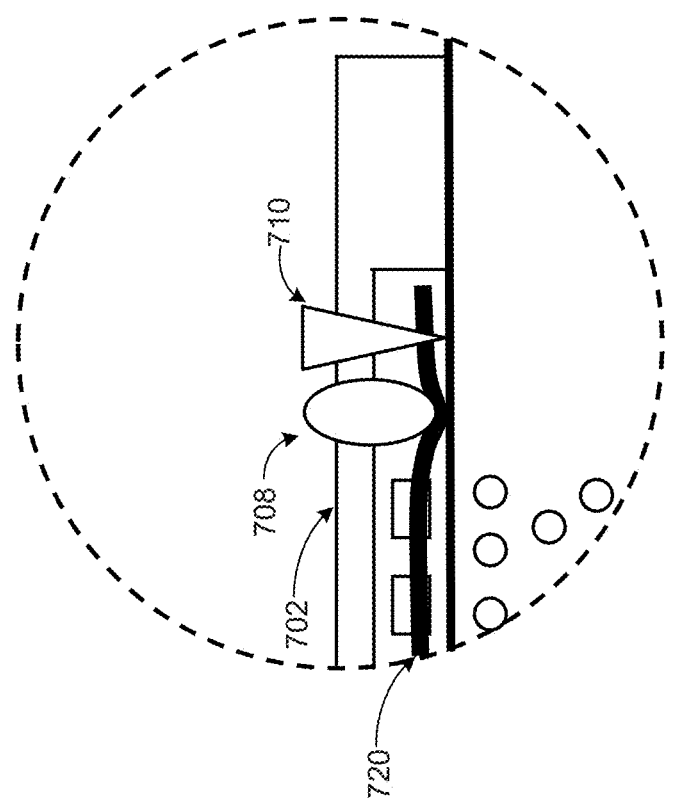
FIG. 7 illustrates an example activation of a cutting blade, all arranged in accordance with at least some embodiments as described herein.

FIG. 7 illustrates an example activation of a cutting blade on a probe, arranged in accordance with at least some embodiments as described herein. As previously described, if a surgeon determines, based on a displayed perfusion map, that a potential cut line has adequate perfusion, then the surgeon may proceed to perform a cut at the potential cut line employing a cutting blade 710 on the sliding member 702. The compression ring 708 which may be adjacent to the cutting blade 710 may be temporarily activated to apply pressure to the intestinal tissue 720 to stabilize and hold the intestinal tissue 720 in place for cutting. The cutting blade 710 may subsequently be activated to cut through the intestinal tissue 720. After cutting the intestinal tissue at a selected cut line, the probe and sliding member may be removed and reinserted at a second location in the intestines to select another cut line for completing the anastomosis procedure.

While embodiments have been discussed above using specific examples, components, and configurations, they are intended to provide a general guideline to be used for providing a device for simulating and selecting an anastomosis cut line. These examples do not constitute a limitation on the embodiments, which may be implemented using other components, modules, and configurations using the principles described herein. Furthermore, actions discussed above may be performed in various orders, especially in an interlaced fashion.

According to some examples, the present disclosure generally describes a probe cutting device for selecting a location to cut intestines for anastomosis. The probe cutting device may include a substantially cylindrical probe having a substantially rounded distal tip, a plurality of light emitters positioned circumferentially on an external surface of the probe in a vicinity of a distal end of the probe, a sliding member having a hollow center, the sliding member configured to fit concentrically around the probe and to slide axially along a longitudinal axis of the probe, and a plurality of photodetectors positioned circumferentially around an interior surface of the sliding member, where the plurality of photodetectors are oriented to face the plurality of light emitters when the sliding member is slid over the probe.

According to some examples, the probe may be configured to be inserted through an incision in a portion of intestinal wall tissue into a lumen of intestines such that the intestinal wall tissue surrounds the external surface of the probe. A diameter of the probe may be selected such that the probe may be in contact with the intestinal wall tissue. The sliding member may be configured to slide over the probe and the intestines such that the intestinal wall tissue passes between the probe and the sliding member. The sliding member may include a slit opening along a longitudinal axis to enable mesenteric tissue attached to the intestinal wall tissue to exit the sliding member.

According to some examples, the probe cutting device may include a first mechanical stop on the sliding member configured to indicate a fully forward sliding position and a second mechanical stop on the sliding member configured to indicate a fully retracted sliding position of the sliding member in relation to the probe. The sliding member may be composed of a transparent material. The sliding member may be composed of a polymer material. The polymer material may include one or more of polyethylene, polypropylene, polyester, polyurethane, polystyrene, polysulfone and/or polyethersulfone.

According to some examples, the plurality of light emitters may be Light Emitting Diode (LED) emitters configured to emit light having a wavelength configured to transmit through intestinal wall tissue. The LED emitters include at least one red LED die and at least one infrared (IR) LED die. The LED emitters may be configured to transmit light in a range from about 550 nm to about 900 nm.

According to some examples, the probe cutting device may include a compression ring configured to fit around a circumference of the sliding member and configured to be compressed for applying pressure to intestinal wall tissue. The compression ring may be compressed around a potential cut line location in the intestinal wall tissue to simulate cutting by applying a pressure greater than an arterial and venous pressure in the intestinal wall tissue. The plurality of photodetectors may be configured to detect a light pattern transmitted by the light emitters before compression of the compression ring and during compression of the compression ring at the potential cut line location, and to transmit the detected light patterns to an external computing device.

According to some examples, the external computing device may be configured to generate a perfusion map based on the transmitted detected light patterns. The perfusion map may be displayed on a monitor associated with the external computing device as a two-dimensional map of an unrolled circumference of the intestinal wall tissue.

According to other examples, the probe cutting device may include a cutting blade configured to cut along a selected cut line location in intestinal wall tissue. The cutting blade may be a rotatable cutting blade.

According to other examples, the present disclosure describes a method of simulating a cut line in intestinal wall tissue and cutting along the cut line for achieving anastomosis. The method may include making an initial incision in intestinal wall tissue near a location of tissue to be removed from intestines, inserting a probe including a plurality of light emitters positioned circumferentially on an external surface of the probe in a vicinity near a distal end of the probe through the incision into a lumen of the intestines such that the intestinal wall tissue surrounds the external surface of the probe and covers the plurality of light emitters, sliding a sliding member over the probe and an external surface of the intestinal wall tissue to a potential cut line at a location where a plurality of photodetectors positioned circumferentially around an interior surface of the sliding member are oriented to face the plurality of light emitters, compressing a compression ring positioned around a circumference of the member to simulate cutting along the potential cut line, transmitting a light pattern detected at the potential cut line to an external computing device, generating a perfusion map based on the detected light pattern at the potential out line, and if the perfusion map indicates that the potential cut line is an acceptable cut line, activating a cutting blade positioned next to the compression ring on the sliding member to cut the intestinal wall tissue along the potential cut line.

According to some examples, the method may include passing mesenteric tissue attached to the intestinal wall tissue through an opening along a longitudinal axis of the sliding member. The method may include configuring the plurality of light emitters to be Light Emitting Diode (LED) emitters that emit light in a range from about 550 nm to about 850 nm. The method may include configuring each of the LED emitters to emit light from at least one red die and at least one IR die.

According to other examples, the method may include configuring the LED emitters to alternate emission of light from the red die and the IR die. The method may include configuring the LED emitters and the photodetectors to multiplex emission and detection of light. The method may include generating a baseline perfusion map before compression of the compression ring around the potential cut line such that the perfusion map generated during compression of the compression ring may be calculated relative to the baseline perfusion map. The method may include compressing the compression ring to simulate cutting by applying a pressure greater than an arterial and a venous pressure of the intestinal wall tissue.

According to other examples, the method may include releasing the compression ring after compression and generation of the perfusion map to prevent ischemia of the intestinal wall tissue. The method may include if the perfusion map indicates that the potential cut line may be an acceptable cut line, temporarily compressing the compression ring to support the intestinal wall tissue while cutting the intestinal wall tissue along the potential cut line.

According to other examples, the method may include if the perfusion map indicates that the potential cut line may be not an acceptable cut line, sliding the sliding member slightly forward to a new potential out line, compressing the compression ring around the intestinal wall tissue at the new potential cut line, generating a new perfusion map at the new potential cut line, and if the new perfusion map indicates that the new potential cut line may be an acceptable cut line, activating the cutting blade to cut the intestinal wall tissue along the new potential cut line.

According to further examples, the present disclosure also describes a system for simulating a cut line in intestinal wall tissue and cutting along the cut line for achieving anastomosis. The system may include a substantially cylindrical probe having a substantially rounded distal tip, a plurality of light emitters positioned circumferentially on an external surface of the probe in a vicinity of a distal end of the probe, a sliding member having a hollow center, the sliding member configured to fit concentrically around the probe and to slide axially along a longitudinal axis of the probe, a plurality of photodetectors positioned circumferentially around an interior surface of the sliding member, where the plurality of photodetectors may be oriented to face the plurality of light emitters when the sliding member is slid over the probe, an external computing device configured to generate a perfusion map based on a detected light pattern, and a monitor associated with the external computing device configured to display the generated perfusion map.

According to some examples, the probe may be configured to be inserted through an incision in a portion of intestinal wall tissue into a lumen of intestines such that the intestinal wall tissue surrounds the external surface of the probe. A diameter of the probe may be selected such that the probe may be in contact with the intestinal wall tissue. The sliding member may be configured to slide over the probe and the intestines such that the intestinal wall tissue passes between the probe and the sliding member.

According to other examples, the sliding member may include a slit opening along a longitudinal axis to enable mesenteric tissue attached to the intestinal wall tissue to exit the sliding member.

According to further examples, the system may also include a first mechanical stop on the sliding member configured to indicate a fully forward sliding position, and a second mechanical stop on the sliding member configured to indicate a fully retracted sliding position of the sliding member in relation to the probe. The sliding member may be composed of a transparent material. The sliding member may be composed of a polymer material. The polymer material may include one or more of polyethylene, polypropylene, polyester, polyurethane, polystyrene, polysulfone and/or polyethersulfone.

According to further examples, the plurality of light emitters may be Light Emitting Diode (LED) emitters configured to emit light having a wavelength configured to transmit through the intestinal wall tissue. The LED emitters include at least one red LED die and at least one infrared (IR) LED die. The LED emitters may be configured to transmit light in a range from about 550 nm to about 900 nm.

According to further examples, the system may also include a compression ring configured to fit around a circumference of the sliding member and configured to be compressed for applying pressure to intestinal wall tissue. The compression ring may be compressed around a potential cut line location in the intestinal wall tissue to simulate cutting by applying a pressure greater than an arterial and venous pressure in the intestinal wall tissue. The plurality of photodetectors may be configured to detect a light pattern transmitted by the LED emitters before compression of the compression ring and during compression of the compression ring at the potential cut line location, and to transmit the detected light patterns to the external computing device to generate the perfusion map based on the transmitted detected light patterns.

According to other examples, the perfusion map may be displayed on the monitor as a two-dimensional map of an unrolled circumference of the intestinal wall tissue. A baseline perfusion map may be generated before compression of the compression ring around the potential cut line such that the perfusion map generated during compression of the compression ring may be calculated relative to the baseline perfusion map.

According to yet other examples, the system may also include a cutting blade configured to cut along a selected cut line location in the intestinal wall tissue. The cutting blade may be a rotatable cutting blade.

There is little distinction left between hardware and software implementations of aspects of systems; the use of hardware or software is generally (but not always, in that in certain contexts the choice between hardware and software may become significant) a design choice representing cost vs. efficiency tradeoffs. There are various vehicles by which processes and/or systems and/or other technologies described herein may be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for mainly hardware and/or firmware vehicle; if flexibility is paramount, the implementer may opt for mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g. as one or more programs running on one or more microprocessors), as firmware, or as virtually any combination thereof, and that designing the circuitry and/or writing the code for the software and/or firmware would be well within the skill of one of skill in the art in light of this disclosure.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive (HDD), a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors e.g., feedback for sensing position and/or velocity of gantry systems; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should he interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method to simulate a cut line in intestinal wall tissue and cut along the cut line for achieving anastomosis, the method comprising:
   making an initial incision in the intestinal wall tissue near a location of tissue to be removed from intestines;
   inserting a probe including a plurality of light emitters positioned circumferentially on an external surface of the probe in a vicinity near a distal end of the probe through the incision into a lumen of the intestines such that the intestinal wall tissue surrounds the external surface of the probe and covers the plurality of light emitters;
   sliding a sliding member over the probe and an external surface of the intestinal wall tissue to a potential cut line at a location where a plurality of photodetectors positioned circumferentially around an interior surface of the sliding member are oriented to face the plurality of light emitters;
   compressing a compression ring positioned around a circumference of the sliding member to simulate cutting along the potential cut line;
   transmitting a light pattern detected at the potential cut line to an external computing device;
   generating a perfusion map based on the detected light pattern at the potential cut line; and
   if the perfusion map indicates that the potential cut line is an acceptable cut line, activating a cutting blade positioned next to the compression ring on the sliding member to cut the intestinal wall tissue along the potential cut line and temporarily compressing the compression ring to support the intestinal wall tissue while the cutting blade is cutting the intestinal wall tissue.

2. The method of claim 1, further comprising:
   configuring the plurality of light emitters to be Light Emitting Diode (LED) emitters that emit light in a range from about 550 nm to about 850 nm.

3. The method of claim 2, further comprising:
   configuring each of the LED emitters to emit light from at least one red die and at least one IR die.

4. The method of claim 3, further comprising:
   configuring the LED emitters to alternate emission of light from the at least one red die and the at least one IR die.

5. The method of claim 3, further comprising:
   configuring the LED emitters and the plurality of photodetectors to multiplex emission and detection of light.

6. The method of claim 1, further comprising:
   releasing the compression ring after compression and generation of the perfusion map to prevent ischemia of the intestinal wall tissue.

7. The method of claim 1, further comprising:
   if the perfusion map indicates that the potential cut line is not the acceptable cut line, sliding the sliding member slightly forward to a new potential cut line;
   compressing the compression ring around the intestinal wall tissue at the new potential cut line;
   generating a new perfusion map at the new potential cut line; and
   if the new perfusion map indicates that the new potential cut line is the acceptable cut line, activating the cutting blade to cut the intestinal wall tissue along the new potential cut line.

* * * * *

UNITED STATES PATENT AND TRADEMARK OFFICE
CERTIFICATE OF CORRECTION

PATENT NO. : 9,713,480 B2
APPLICATION NO. : 14/356391
DATED : July 25, 2017
INVENTOR(S) : Leschinsky et al.

It is certified that error appears in the above-identified patent and that said Letters Patent is hereby corrected as shown below:

In the Specification

In Column 1, Line 60, delete "to lit concentrically" and insert -- to fit concentrically --, therefor.

In Column 2, Line 11, delete "potential out line" and insert -- potential cut line --, therefor.

In Column 3, Lines 36-37, delete "simulated. cut line, and" and insert -- simulated cut line, and --, therefor.

In Column 4, Line 17, delete "tissue length, A" and insert -- tissue length. A --, therefor.

In Column 5, Lines 65-66, delete "compression 308" and insert -- compression ring 308 --, therefor.

In Column 7, Line 28, delete "a sate and" and insert -- a safe and --, therefor.

In Column 7, Line 41, delete "potential out line" and insert -- potential cut line --, therefor.

In Column 10, Lines 31-32, delete "the member" and insert -- the sliding member --, therefor.

In Column 10, Lines 35-36, delete "potential out line, and" and insert -- potential cut line, and --, therefor.

In Column 11, Line 6, delete "potential out line, compressing" and insert -- potential cut line, compressing --, therefor.

In Column 13, Line 47, delete "control motors e.g., feedback" and insert -- control motors (e.g., feedback --, therefor.

Signed and Sealed this
Thirty-first Day of October, 2017

Joseph Matal
*Performing the Functions and Duties of the
Under Secretary of Commerce for Intellectual Property and
Director of the United States Patent and Trademark Office*

In Column 14, Line 43, delete "should he interpreted" and insert -- should be interpreted --, therefor.

In Column 14, Line 54, delete "will further" and insert -- will be further --, therefor.